(12) United States Patent
Nagoshi et al.

(10) Patent No.: US 8,763,447 B2
(45) Date of Patent: Jul. 1, 2014

(54) ULTRAVIOLET CURING RESIN PROPERTY MEASURING APPARATUS

(75) Inventors: Toshiyuki Nagoshi, Hachioji (JP); Jun Koshoubu, Hachioji (JP); Mitsuo Watanabe, Tokyo (JP); Takashi Inoue, Tokyo (JP); Shigeru Ito, Tokyo (JP)

(73) Assignees: JASCO Corporation, Hachioji-shi, Tokyo (JP); JASCO International Co., Ltd., Hachioji-shi, Tokyo (JP)

( * ) Notice: Subject to any disclaimer, the term of this patent is extended or adjusted under 35 U.S.C. 154(b) by 520 days.

(21) Appl. No.: 13/085,563

(22) Filed: Apr. 13, 2011

(65) Prior Publication Data
US 2011/0252871 A1    Oct. 20, 2011

(30) Foreign Application Priority Data
Apr. 14, 2010    (JP) .................................. 2010-93089

(51) Int. Cl.
*G01N 11/14* (2006.01)

(52) U.S. Cl.
USPC ........................................................ 73/54.02

(58) Field of Classification Search
USPC ....................................................... 73/54.02
See application file for complete search history.

(56) References Cited

U.S. PATENT DOCUMENTS

| | | | |
|---|---|---|---|
| 4,435,080 A * | 3/1984 | Maly et al. ..................... 356/426 |
| 4,601,195 A * | 7/1986 | Garritano ....................... 73/54.34 |
| 5,520,042 A * | 5/1996 | Garritano et al. ............. 73/54.02 |
| 5,905,196 A * | 5/1999 | Parshall ......................... 73/54.31 |
| 6,988,393 B2 * | 1/2006 | Feustel .......................... 73/54.39 |
| 6,992,759 B2 * | 1/2006 | Nakayama et al. ........... 356/244 |
| 2004/0226349 A1 * | 11/2004 | Feustel ........................ 73/54.02 |
| 2007/0193343 A1 * | 8/2007 | Liberatore et al. ........... 73/54.33 |

FOREIGN PATENT DOCUMENTS

| | | |
|---|---|---|
| JP | 06-242005 | 9/1994 |
| JP | 2005-098951 | 4/2005 |

OTHER PUBLICATIONS

Japanese Patent Abstract Publication 06-242005 published Sep. 2, 1994, including machine translation of claims and description, five pages.
Japanese Patent Abstract Publication 2005-098951 published Apr. 14, 2005 including machine translation of claims and description, twelve pages.

* cited by examiner

*Primary Examiner* — Hezron E Williams
*Assistant Examiner* — Mark A Shabman
(74) *Attorney, Agent, or Firm* — Rankil, Hill & Clark LLP (57) ABSTRACT

Measuring apparatus comprises a rotating plate 17, a torque detection plate 18 disposed on a same axis parallel to the plate 17 with a given gap, a torque sensor about the plate 18 through the specimen held between two plates. The plate 18 is a total reflection prism which is made from a material that has a greater refractive index than the specimen and transmits UV and infrared light. An ultraviolet beam is directed onto the specimen through the prism. An infrared beam is directed into the prism. The infrared beam emerging from the prism after total reflection from the interface between the prism and the specimen is detected. A signal processor analyzes the infrared absorption spectrum of the specimen on the basis of the infrared beam. While the viscosity of the specimen in the curing process is measured, the signal processor simultaneously measures the infrared absorption spectrum.

7 Claims, 6 Drawing Sheets

FIG. 6

ULTRAVIOLET CURING RESIN PROPERTY MEASURING APPARATUS

RELATED APPLICATIONS

This application claims the priority of Japanese Patent Application No. 2010-93089 filed on Apr. 14, 2010, which are incorporated herein by reference.

FIELD OF THE INVENTION

The present invention relates to apparatuses for measuring a change in the infrared absorption spectrum and the viscosity or viscoelasticity of ultraviolet curing resins, which cure under ultraviolet irradiation and are used as adhesives, encapsulants, paints and so on, during their curing process.

BACKGROUND OF THE INVENTION

Ultraviolet Curing Resin

Ultraviolet curing resins have a property of turning from liquid to crosslinked polymer under ultraviolet irradiation and have been used as adhesives, encapsulants, paints, coating agents, and so on.

When an ultraviolet curing resin is used, the user adjusts the amount of ultraviolet irradiation used for curing. It is important to know in advance the correct curing rate of the resin with respect to ultraviolet irradiation. However, since a cured resin does not dissolve in any type of solvent, a limited number of analytical methods can be applied.

Absorption Spectrum Measurement

Known methods of determining the curing rate of a resin measure a change in the infrared absorption spectrum by an infrared spectrophotometer in the curing process; in particular, the attenuated total reflection (ATR) method has been used often. In the ATR method, a specimen is kept in contact with a total reflection prism; an infrared beam is directed into the prism to cause multiple reflections at the interface; and the infrared absorption spectrum attenuated during the multiple reflections is measured.

With the use of the ATR method, the absorption spectrum is conventionally measured in real time in the curing process (see Japanese Unexamined Patent Application Publication No. Hei-06-242005). The infrared spectrophotometer described in this publication uses a cell chamber in which the ultraviolet curing resin is injected. The cell chamber is penetrated by a total reflection prism formed like plate at center of the chamber, and ultraviolet irradiation windows are disposed on the chamber in front of and behind the total reflection prism. The resin injected in the cell chamber cures under ultraviolet irradiation from the windows. An infrared beam for spectrum measurement is incident on the prism from one end and is guided to the other end by multiple reflections from the interface between the prism and the resin. In that process, the infrared beam is attenuated. The infrared beam emerging from the other end of the prism is detected by a spectrum analysis means. In that way, the infrared absorption spectrum is measured while the resin is curing.

Viscoelasticity Evaluation

As a method of evaluating the viscosity or viscoelasticity of a specimen in regard to the deformation and flow of matter (rheology), a rotational viscometer method is stipulated in the Japanese Pharmacopeia, which is a reference work for pharmaceutical drug specifications, for example. The specimen is held between a pair of flat discs having the same axis of rotation; one disc is rotated; and a torque exerted on the other disc is measured. The viscosity or viscoelasticity of the specimen is calculated on the basis of the measured torque. A known apparatus uses the rotational viscometer method and further measures time-dependent changes in the viscosity or viscoelasticity of the specimen under ultraviolet irradiation (see page 3 of Japanese Unexamined Patent Application Publication No. 2005-98951).

In the rotational viscometer described in this publication, light is directed onto the specimen through a lower flat disc made of silica glass. After an upper flat disc is rotated, irradiation starts, and time-dependent changes in the torque exerted on the lower flat disc are measured. A time point at which the torque increases is read to determine the cumulative amount of ultraviolet light at which curing starts and other data items.

The absorption spectrum and the viscosity or viscoelasticity in the curing process have been measured separately by using different measuring apparatuses, and the curing rate of the resin has been estimated accordingly.

When both the infrared spectrophotometer and the rotational viscometer are used, a specimen of the ultraviolet curing resin must be placed in the infrared spectrophotometer for measuring the absorption spectrum in the curing process under ultraviolet irradiation, and another specimen must be placed in the rotational viscometer for measuring the viscosity or viscoelasticity. The measurement by two different apparatuses increases the number of tasks that must be performed, increasing the load on the person doing the measurement. Different specimens must be prepared for different measuring apparatuses.

The use of ultraviolet curing resins as coating agents has been widespread in recent years, and there is an increasing demand for evaluating viscoelasticity by using a layer of ultraviolet curing resin of about 10 μm thick. To measure the viscosity or viscoelasticity of that thin layer with the rotational viscometer described above, the gap between the flat discs must be adjusted so that the parallelism of one flat disc with respect to the other flat disc satisfies a given precision requirement. However, there has not yet been a measuring apparatus that has a function to measure the gap between the flat discs with a high precision in a short time.

SUMMARY OF THE INVENTION

Accordingly, a first object of the present invention is to provide an ultraviolet curing resin property measuring apparatus that can measure the absorption spectrum and the viscosity or viscoelasticity simultaneously in the curing process and can reduce the load on the person doing the measurement. A second object is to provide an ultraviolet curing resin property measuring apparatus that has a function to measure the gap between a pair of flat discs for holding the specimen, with a high precision in a short time.

One of the foregoing objects is achieved in one aspect of the present invention through the provision of an ultraviolet curing resin property measuring apparatus that includes a rotating plate supported rotatably about a center axis, a torque detection plate disposed on the same axis parallel to the rotating plate, with a given gap left between the two plates, and torque detection means for detecting a torque exerted on the torque detection plate through a specimen of an ultraviolet curing resin held between the rotating plate and the torque detection plate when the rotating plate is turned. The measuring apparatus determines the viscosity or viscoelasticity of the specimen on the basis of the detected torque.

Either the rotating plate or the torque detection plate is a total reflection prism made from a material that has a greater refractive index than the ultraviolet curing resin and transmits ultraviolet light and infrared light.

The measuring apparatus also includes ultraviolet irradiation means disposed on the other side of the total reflection prism from the specimen, for directing an ultraviolet beam onto the specimen through the total reflection prism, infrared irradiation means for directing an infrared beam into the total reflection prism, infrared detection means for detecting the infrared beam emerging from the total reflection prism after total reflection from the interface between the prism and the specimen, and spectrum analysis means for analyzing the infrared absorption spectrum of the specimen on the basis of infrared beam detected by the infrared detection means. The apparatus can measure the viscosity or viscoelasticity and the infrared absorption spectrum of the ultraviolet curing resin simultaneously in the curing process.

In this structure, either the rotating plate or the torque detection plate, both plates sandwiching the specimen, is a total reflection prism. The beam directed along the axis enters the total reflection prism, travels through the prism, and emerges from the opposite end. Accordingly, the ultraviolet beam coming from the ultraviolet irradiation means and entering the total reflection prism along the axis passes through the prism and hits the specimen of the ultraviolet curing resin held between the rotating plate and the torque detection plate. Therefore, the viscosity or viscoelasticity of the specimen can be measured while the ultraviolet beam coming from the ultraviolet irradiation means is being directed onto the specimen through the total reflection prism. When the beam directed into the total reflection prism travels through the prism, if the incident angle of the beam with respect to the interface of the prism is not smaller than the critical angle, total reflection of the beam occurs at the interface. Since the selected total reflection prism has a greater refractive index than the ultraviolet curing resin, if the infrared beam hits the interface between the ultraviolet curing resin and the total reflection prism with an incident angle not smaller than the critical angle, total reflection of the infrared beam occurs in the prism. Accordingly, the infrared absorption spectrum can be measured by the ATR method that uses infrared attenuation in total reflection from the interface between the prism and the specimen. Since the absorption spectrum and the viscosity or viscoelasticity can be measured simultaneously in the curing process, the load on the person doing the measurement can be reduced, which means that the first object is achieved.

One of the foregoing objects is achieved in another aspect of the present invention through the provision of an ultraviolet curing resin property measuring apparatus that includes a rotating plate supported rotatably about a center axis, a torque detection plate disposed on the same axis parallel to the rotating plate with a given gap left between the two plates, and torque detection means for detecting a torque exerted on the torque detection plate through a specimen of an ultraviolet curing resin held between the rotating plate and the torque detection plate when the rotating plate is turned. The measuring apparatus determines the viscosity or viscoelasticity of the specimen on the basis of the detected torque.

Either the rotating plate or the torque detection plate is a total reflection prism made from a material that has a greater refractive index than the ultraviolet curing resin and transmits infrared light, and the other plate is an ultraviolet transmitting plate made from a material that transmits ultraviolet light.

The measuring apparatus also includes ultraviolet irradiation means disposed on the other side of the ultraviolet transmitting plate from the specimen, for directing an ultraviolet beam onto the specimen through the ultraviolet transmitting plate, infrared irradiation means for directing an infrared beam into the total reflection prism, infrared detection means for detecting the infrared beam emerging from the total reflection prism after total reflection from the interface between the prism and the specimen, and spectrum analysis means for analyzing the infrared absorption spectrum of the specimen on the basis of the infrared beam detected by the infrared detection means. The measuring apparatus can measure the viscosity or viscoelasticity and the infrared absorption spectrum of the ultraviolet curing resin simultaneously in the curing process.

Since the rotating plate and torque detection plate, both plates sandwiching the specimen, are configured by a combination of the total reflection prism and the ultraviolet transmitting plate, the effect described earlier can be obtained by directing an ultraviolet beam onto the specimen through the ultraviolet transmitting plate and measuring the infrared absorption spectrum by the ATR method by using the total reflection prism. The ability to measure the absorption spectrum and the viscosity and viscoelasticity simultaneously in the curing process helps to reduce the load on the person doing the measurement.

According to the present invention, it is preferred that the composition of the total reflection prism be ZnS.

It is also preferred in the present invention that the total reflection prism be disposed such that it can move from a position on the optical path of the infrared beam directed from the infrared irradiation means, to a position not on the optical path.

This structure allows the total reflection prism to be moved onto the optical path of the infrared beam for the ATR spectrum measurement and to be moved away from the optical path for spectrum measurement by the external reflection method. Either of the two infrared absorption spectrum measurement modes can be selected properly: attenuated total reflection (ATR) measurement mode and external reflection measurement mode.

It is also preferred in the present invention that the infrared beam of total reflection from the interface between the total reflection prism and the specimen be interfering infrared light (infrared light from an interferometer).

One of the foregoing objects is achieved in still another aspect of the present invention through the provision of an ultraviolet curing resin property measuring apparatus that includes a rotating plate supported rotatably about a center axis, a torque detection plate that is disposed on the same axis parallel to the rotating plate with a given gap left between the two plates, and torque detection means for detecting a torque exerted on the torque detection plate through a specimen of an ultraviolet curing resin held between the rotating plate and the torque detection plate when the rotating plate is turned. The measuring apparatus measures the viscosity or viscoelasticity of the specimen on the basis of the detected torque.

Either the rotating plate or the torque detection plate is a light transmitting plate made from a material that transmits ultraviolet light and infrared light.

The measuring apparatus also includes ultraviolet irradiation means disposed on the other side of the light transmitting plate from the specimen, for directing an ultraviolet beam onto the specimen through the light transmitting plate, infrared irradiation means for directing an infrared beam into the light transmitting plate, and gap detection means for detecting the gap between the rotating plate and the torque detection plate on the basis of the phase difference between an infrared beam reflected from the interface between the light transmitting plate and the specimen and an infrared beam reflected from the back side of the specimen through the interface. The measuring apparatus adjusts the gap by using the gap detection means and measures the viscosity or viscoelasticity of the ultraviolet curing resin in the curing process.

In this structure, since the light transmitting plate made from a material that transmits both infrared light and ultraviolet light is used as either the rotating plate or the torque detection plate, when an ultraviolet beam is directed onto the specimen through the light transmitting plate, and an infrared beam is directed toward the same light transmitting plate, the gap between the plates can be measured based on the difference in optical path length between a beam reflected from the interface between the plate and the specimen, that is, the front side of the specimen, and a beam reflected from the back side of the specimen, which interfere with each other. With this method, a gap of about 10 µm can be measured with a high precision. Accordingly, the second object of measuring the gap between a pair of plates holding the specimen, with a high precision in a short time and measuring the viscosity or viscoelasticity of a layer of ultraviolet curing resin of about 10 µm thick in the curing process can be achieved.

It is preferred in the present invention that the composition of the light transmitting plate be KBr, NaCl, KCl, BaF2, or CaF2.

An ultraviolet curing resin property measuring apparatus according to the present invention can measure the absorption spectrum and the viscosity or viscoelasticity simultaneously in the curing process and can reduce the load on the person doing the measurement. An ultraviolet curing resin property measuring apparatus according to the present invention can measure the gap between a pair of plates holding the specimen, with a high precision in a short time.

DESCRIPTION OF THE PREFERRED EMBODIMENTS

Ultraviolet curing resin property measuring apparatuses according to embodiments of the present invention will be described below with reference to the drawings.

First Embodiment

A property measuring apparatus 10 according to a first embodiment has both a viscometric function and an infrared absorption spectrum measurement function. The measuring apparatus 10 measures the viscosity or viscoelasticity and the infrared absorption spectrum of a specimen of, especially, an ultraviolet curing resin, such as urethane acrylate or epoxy acrylate, while the specimen is being cured under ultraviolet irradiation.

Figure 1:
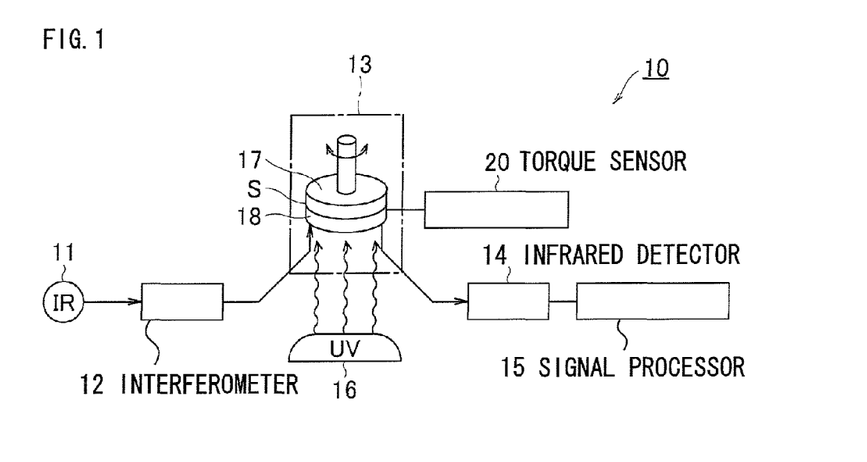
FIG. 1 is a block diagram schematically illustrating the configuration of an ultraviolet curing resin property measuring apparatus according to a first embodiment of the present invention.

As shown in FIG. 1, the property measuring apparatus 10 includes an infrared light source 11, which corresponds to infrared irradiation means in the present invention, an interferometer 12 which obtains interfering infrared light from infrared beams, a specimen holding unit 13 into which the interfering infrared light is directed from the interferometer 12, an infrared detector 14 which detects the intensity of interfering infrared light emerging from the specimen holding unit 13, a signal processor (spectrum analysis means) 15 which reads a light intensity signal from the infrared detector 14 and analyzes the infrared absorption spectrum by performing known signal processing such as Fourier transformation, and an ultraviolet light source 16, which corresponds to ultraviolet irradiation means in the present invention.

Here, a Michelson interferometer is used as the interferometer 12. This, however, does not mean that the structure of the interferometer 12 is limited to that type. The infrared detector 14 corresponds to infrared detection means in the present invention, and an MCT detector is used in this embodiment.

Figure 2:
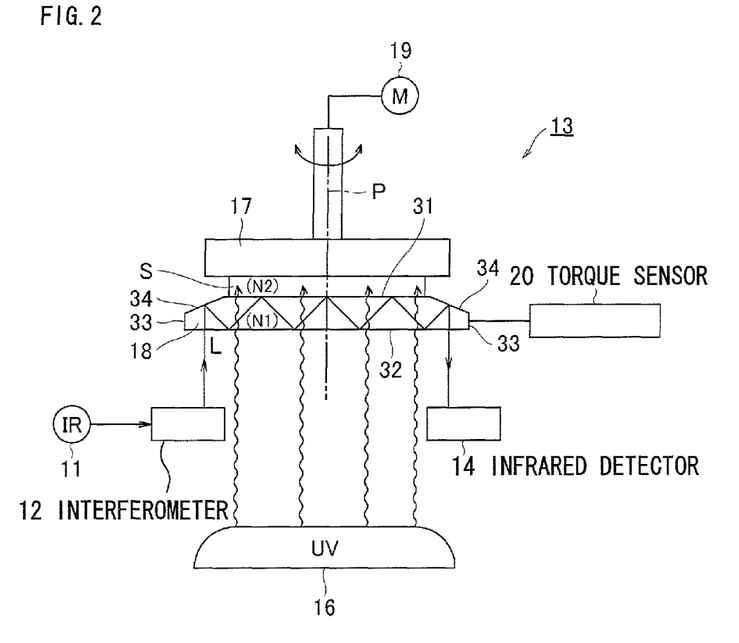
FIG. 2 is a view showing the arrangement of a rotating plate, a specimen, and a total reflection prism in the measuring apparatus.

FIG. 2 shows a magnified view of the specimen holding unit 13 in FIG. 1. As shown in the figure, the specimen holding unit 13 includes a rotating plate 17 and a torque detection plate 18, and a specimen S of an ultraviolet curing resin is held between the two plates.

The rotating plate 17 is supported by a main body, not shown, in such a manner that it can rotate about a center axis P. The rotating plate 17 is usually turned by a rotating driving unit 19, such as an electric motor M, connected to the rotating plate 17 through a power transmission shaft. The type of the rotating driving unit 19 and the power transmission method from the rotating driving unit 19 to the rotating plate 17 are not particularly restricted. The rotating plate 17 should have a single rotating direction at least. A rotating driving unit that can rotate the rotating plate 17 in two directions alternately at a given frequency may be adopted in this embodiment.

The torque detection plate 18 is aligned with the rotating plate 17 on the same axis P and is supported to be parallel to the rotating plate 17 with a given gap left between them. The torque detection plate 18 has a torque sensor 20, which corresponds to torque detection means. When the electric motor M rotates the rotating plate 17, the torque sensor 20 detects a torque T occurring on the torque detection plate 18 through the specimen S. The viscosity or viscoelasticity of the specimen S is measured on the basis of the torque T. The torque sensor 20 may be a contact-type torque sensor or a non-contact-type torque sensor such as a magnetostrictive sensor. The torque sensor may also detect the torque T exerted on the torque detection plate 18 on the basis of the torsion of the spring.

What distinguishes the present invention is that both the infrared absorption spectrum and the viscosity or viscoelasticity can be measured simultaneously in the curing process of the ultraviolet curing resin. Accordingly, for that purpose, a total reflection prism is used as the torque detection plate 18 in the embodiment, as shown in FIG. 2. In this embodiment, the total reflection prism will be denoted by a reference number 18, which also denotes the torque detection plate.

The total reflection prism 18 is made from a material that has a refractive index N1, which is greater than a refractive index N2 (about 1.3 to 1.4) of the ultraviolet curing resin (N2<N1), and transmits both ultraviolet light and infrared light. The refractive index N1 of the total reflection prism 18 should be 2.0 or greater, preferably 2.3 or greater, for example. One material that has these properties is diamond, for example. Diamond is an optical material that transmits light well in a wide range of wavelengths, from ultraviolet to infrared (0.2 to 80 μm), and has a refractive index of 2.42.

Figure 3A:
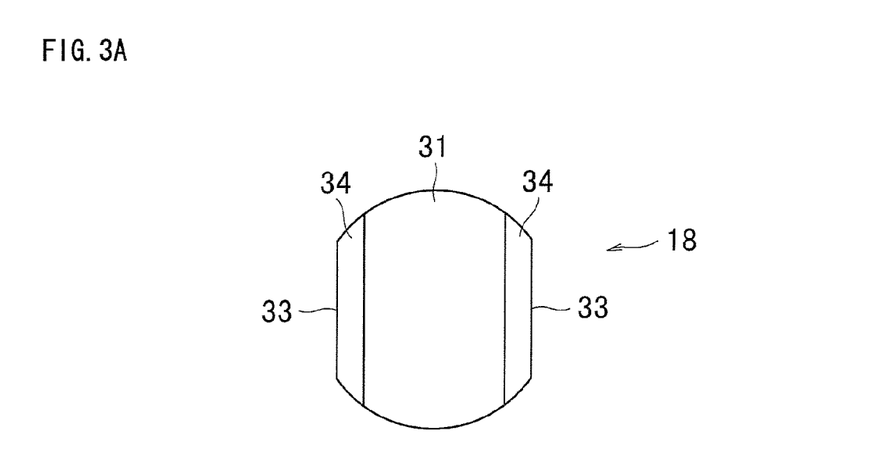
FIG. 3A is a plan view of the total reflection prism.

The total reflection prism 18 is almost disc-shaped. Here, the side of the total reflection prism 18 that is in contact with the specimen S will be referred to as a front side 31, and the opposite side will be referred to as a back side 32. As shown in the plan view in FIG. 3A, the circular outer edge of the total reflection prism 18 has two parallel cut-off faces 33. As shown in the longitudinal sectional view in FIG. 3B, sloped faces 34 are formed on ridges between the cut-off faces 33 and the front side 31. The sloped faces 34 are covered by an aluminum layer formed by vapor deposition.

Figure 3B:
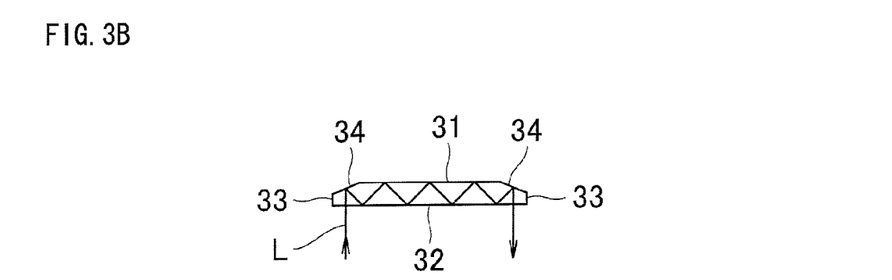
FIG. 3B is a longitudinal sectional view of the total reflection prism.

The angles formed by the sloped faces 34 and the front side 31 are each set to 22.5° so that, like the optical path L shown in FIG. 3B, a beam orthogonally entering from the back side 32 repeats total reflection from the front side 31 and the back side 32 with an incident angle of 45° in the prism. In this embodiment, a prism of 35 mm in diameter and 3.5 mm in thickness is used. A rectangular prism of 10 mm in width, 30 to 60 mm in length, and 3 mm in thickness, for example, can also be used as a multiple total reflection prism.

The optical path L between the interferometer 12 and the total reflection prism 18 shown in FIG. 2 is formed of optical elements, not shown, such as a reflecting mirror, in such a manner that interfering infrared light from the interferometer 12 hits the back side 32 of the total reflection prism 18. On the optical path L, interfering infrared light enters the total reflection prism 18 from a part of the back side 32 close to one of the cut-off faces 33 and hits the back side 32 in the prism with an incident angle of 45°.

The ultraviolet light source 16 is placed on the other side of the total reflection prism 18 from the specimen S.

Accordingly, interfering infrared light from the interferometer 12 hits the back side 32 of the total reflection prism 18 orthogonally as shown in FIG. 2. The interfering infrared light entering the prism is totally reflected by one of the sloped faces 34 first because of the aluminum layer deposited on the sloped face 34. The reflected interfering infrared light is then totally reflected by the back side 32 with an incident angle of 45°, and the totally reflected interfering infrared light is further totally reflected by the front side 31 with an incident angle of 45°. This incident angle of 45° is greater than the critical angle determined by the refractive index N1 of the total reflection prism 18 and the refractive index N2 of the specimen S. Therefore, interfering infrared light totally reflected by the back side 32 is totally reflected again by the front side 31. Total reflection from the back side 32 and the front side 31 is repeated until the interfering infrared light is reflected by the sloped face 34 on the other end. The interfering infrared light reflected by the sloped face 34 on the other end emerges from the back side 32.

Each time total reflection occurs on the front side 31 of the total reflection prism 18, which is the interface between the total reflection prism 18 and the specimen S, the intensity of the interfering infrared light is attenuated, and the intensity of the attenuated interfering infrared light is detected by the infrared detector 14.

When the intensity detected by the infrared detector 14 becomes stable, a shutter, not shown, provided for the ultraviolet light source 16 opens. An ultraviolet beam from the ultraviolet light source 16 enters the total reflection prism 18 orthogonally from the back side 32 and hits the specimen S on the other side of the total reflection prism 18. The infrared detector 14 continues detecting the interfering infrared light until the accumulated amount of ultraviolet irradiation reaches a given level and starts to cure the resin. When the ultraviolet irradiation starts, the electric motor M starts rotating the rotating plate 17, and the torque sensor 20 detects a torque exerted on the total reflection prism 18, which is the torque detection plate. Like the infrared detector 14, the torque sensor 20 continues torque detection until the resin starts to cure.

According to the present invention, since the torque detection plate is the total reflection prism 18 that transmits ultraviolet light, the viscosity or viscoelasticity of the specimen S can be measured while the specimen S is exposed to ultraviolet irradiation from the ultraviolet light source 16 through the total reflection prism 18. Because the selected total reflection prism 18 also transmits infrared light and has a greater refractive index N1 than the ultraviolet curing resin, the infrared absorption spectrum can be measured by the ATR method utilizing the attenuation of infrared light in total reflection. The ability of measure the infrared absorption spectrum and the viscosity or viscoelasticity simultaneously in the curing process helps to significantly reduce the load on the person doing the measurement. With the ATR method, the infrared absorption spectrum can be measured, irrespective of the thickness of the specimen.

Second Embodiment

Figure 4:
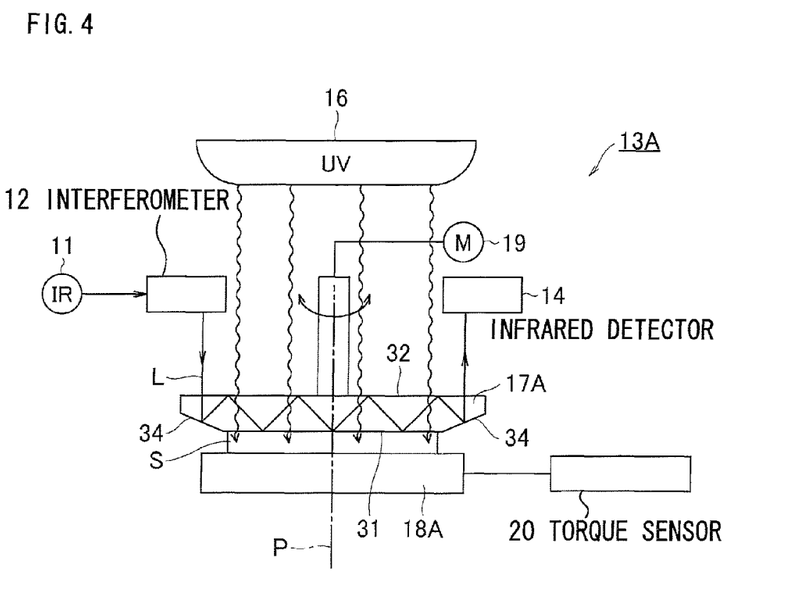
FIG. 4 is a view showing the arrangement of a total reflection prism, a specimen, and a torque detection plate in a second embodiment of the present invention.

A property measuring apparatus according to a second embodiment of the present invention will be described next with reference to FIG. 4.

The property measuring apparatus in this embodiment differs from the property measuring apparatus in the first embodiment just in the structure of the specimen holding unit.

What distinguishes the present invention is that both the infrared absorption spectrum and the viscosity or viscoelasticity can be measured simultaneously in the curing process of the ultraviolet curing resin, as in the first embodiment. A total reflection prism is used as a rotating plate 17A in this embodiment, as shown in FIG. 4. The optical path L of interfering infrared light from the interferometer 12 is directed toward the rotating plate 17A instead of a torque detection plate 18A. A ultraviolet light source 16 is also placed to direct an ultraviolet beam to the rotating plate 17A instead of the torque detection plate 18A. In this embodiment, the total reflection prism will be denoted by a reference number 17A, which also denotes the rotating plate.

The total reflection prism 17A has the same material and the same shape as the total reflection prism 18 in the first embodiment. The total reflection prism 17A is connected to an electric motor M through a power transmission shaft.

While the total reflection prism 17A is being rotated by the electric motor M, interfering infrared light does not hit any of the sloped faces 34 of the prism at some rotation angle about the axis P, interrupting total reflection in the prism. Even in that case, the infrared absorption spectrum can be measured by detecting the attenuated interfering infrared light by the infrared detector 14 just in a period in which the interfering infrared light hits one of the sloped faces 34 of the prism. Accordingly, the apparatus can produce the same effect as the property measuring apparatus in the first embodiment, and the infrared absorption spectrum and the viscosity or viscoelasticity can be measured simultaneously in the curing process.

Another feature of the present invention is that either of two infrared absorption spectrum measurement modes can be selected: the ATR method and the external reflection method. Accordingly, in this embodiment, the total reflection prism 17A, which is the rotating plate, can be moved away from the optical path L of the interfering infrared light from the interferometer 12, in a direction parallel to or orthogonal to the axis P.

In this structure, for the ATR spectrum measurement, the total reflection prism 17A is moved onto the optical path L of the interfering infrared light. For spectrum measurement by the external reflection method, the total reflection prism 17A is moved away from the optical path L of interfering infrared light. In either measurement mode, the infrared absorption spectrum is measured by using interfering infrared light from the interferometer 12. The infrared absorption spectrum measurement mode can be selected from the two options: the ATR measurement mode and the external reflection measurement mode.

Third Embodiment

A property measuring apparatus according to a third embodiment of the present invention will now be described with reference to FIG. 5.

The property measuring apparatus according to the third embodiment differs from the property measuring apparatus in the second embodiment just in the structure of the specimen holding unit.

Figure 5:
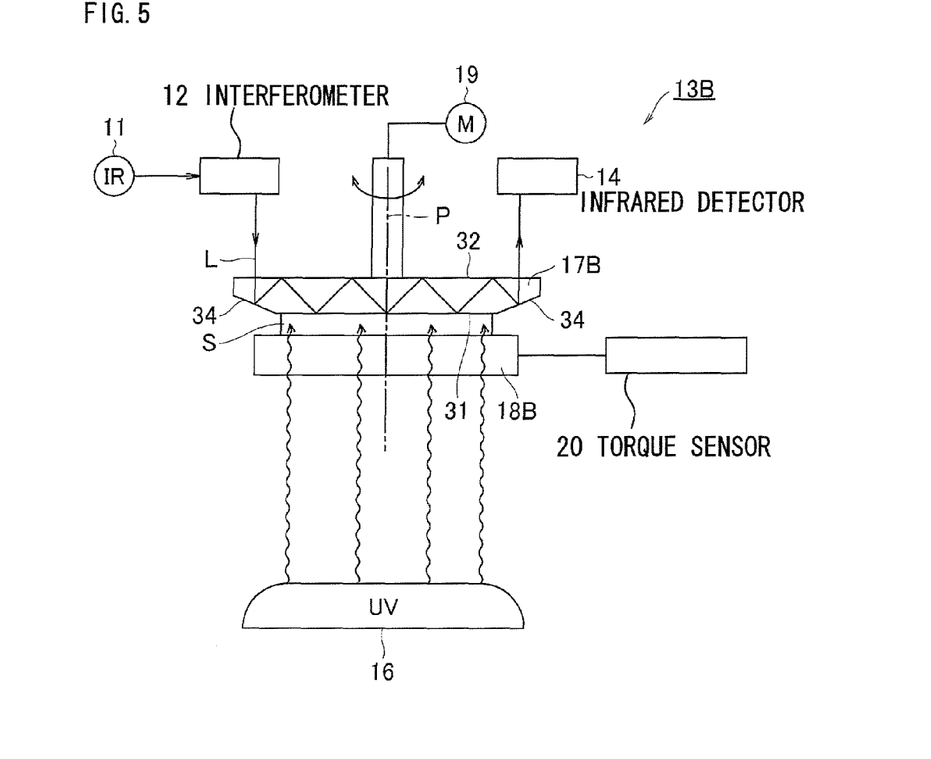
FIG. 5 is a view showing the arrangement of a total reflection prism, a specimen, and an ultraviolet transmitting plate in a third embodiment of the present invention.

As shown in FIG. 5, a total reflection prism 17B is used as a rotating plate. The total reflection prism 17B is made from a material that has a greater refractive index N1 than the ultraviolet curing resin and transmits infrared light. The total reflection prism 17B made, in particular, from polycrystalline zinc sulfide (ZnS) should be adopted. ZnS is an optical material that transmits infrared light (wavelength of 0.4 μm to 12 μm) well and has a refractive index of 2.37.

The total reflection prism 17B in this embodiment may be made of ZnSe, Ge, or diamond, as well as ZnS.

As a torque detection plate, an ultraviolet transmitting plate 18B is used. The ultraviolet light source 16 is disposed on the other side of the ultraviolet transmitting plate 18B from the specimen S and directs an ultraviolet beam onto the specimen S through the ultraviolet transmitting plate 18B.

The combination of the total reflection prism 17B and the ultraviolet transmitting plate 18B can be reversed. Specifically, the ultraviolet transmitting plate 18B may be used as the rotating plate, and the total reflection prism 17B may be used as the torque detection plate.

In the apparatus according to this embodiment, the rotating plate and the torque detection plate that hold the specimen S therebetween are configured by a combination of the total reflection prism 17B and the ultraviolet transmitting plate 18B. Accordingly, if an ultraviolet beam is directed onto the specimen S through the ultraviolet transmitting plate 18B and if the total reflection prism 17B is used to measure the infrared absorption spectrum by the ATR method, the apparatus can produce the same effect as the property measuring apparatus in the first embodiment.

Fourth Embodiment

Figure 6:
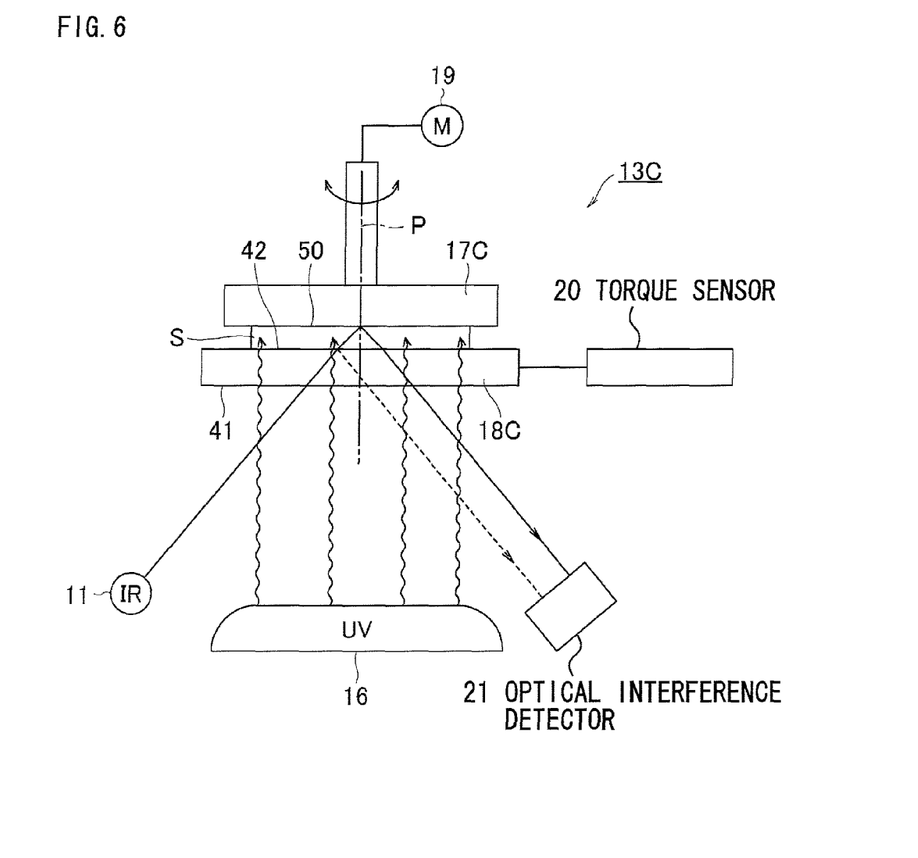
FIG. 6 is a view showing the arrangement of a rotating plate, a specimen, and a light transmitting plate in a fourth embodiment of the present invention.

A property measuring apparatus according to a fourth embodiment of the present invention will be described next with reference to FIG. 6.

The property measuring apparatus in this embodiment differs from the property measuring apparatus in the first embodiment just in the structure of the specimen holding unit and the type of the infrared beam to be used.

What distinguishes the present invention is that the gap between a pair of plates 17C and 18C which hold the specimen S can be measured with a high precision in a short time, and the viscosity or viscoelasticity of a layer of ultraviolet curing resin of about 10 μm thick can be measured in its curing process. In this embodiment, a light transmitting plate 18C made from a material that transmits ultraviolet light and infrared light is used as the torque detection plate. A preferable composition of the material for the light transmitting plate 18C is KBr, NaCl, KCl, BaF2, or CaF2. An infrared light source 11 which directs an infrared beam onto the light transmitting plate 18C and an optical interference detector 21 which detects the reflection of the infrared beam, serving as gap detection means, are also included.

Since an ultraviolet beam is directed to the specimen S through the light transmitting plate 18C, the viscosity or viscoelasticity of the ultraviolet curing resin can be measured in the curing process.

An infrared beam from the infrared light source 11 hits a front side 41 (lower side in FIG. 6) of the light transmitting plate 18C with a given incident angle. The infrared beam travels through the light transmitting plate 18C, and a part of the beam is reflected by a back side 42 (upper side in FIG. 6, in contact with the specimen), and the rest is refracted. The infrared beam reflected by the back side 42 is indicated by a broken line in the figure. The infrared beam refracted by the back side 42 travels through the specimen S and is reflected by the back side of the specimen S, that is, the interface 50 between the specimen S and the rotating plate 17C. The optical interference detector 21 detects optical interference caused by the difference in optical path length between the two reflected beams. The gap between the light transmitting plate 18C and the rotating plate 17C is calculated on the basis of the phase difference between the two reflected beams. In the gap measurement based on the phase difference between the two reflected infrared beams, a gap of about 10 μm can be measured with a high precision. Therefore, the gap between the plates 17C and 18C can be adjusted with a high precision in a short time, and the viscosity or viscoelasticity of a layer of ultraviolet curing resin of about 10 μm thick can be measured in the curing process.

The same effect can be produced by using the light transmitting plate 18C not as the torque detection plate but as the rotating plate in this embodiment. The gap measuring system in this embodiment can be applied to the measuring apparatus in the above mentioned embodiments. For example, by using the light transmitting plate as the rotating plate 17 in FIG. 2, or as the torque detection plate 18A in FIG. 4, or as the ultraviolet transmitting plate 18B in FIG. 5, the gap between the plates can be measured with a high precision.

The total reflection prisms 18, 17A, and 17B in the first to third embodiments are not limited to a multiple total reflection prism and can be a total reflection prism of single reflection. The prism is preferable when the contact surface with the specimen is small.

In the first to third embodiments described above, a measuring apparatus using a Fourier-transform infrared spectrophotometer has been described. However, the present invention can be applied appropriately to a measuring apparatus using a dispersive infrared spectrophotometer.

What is claimed is:

1. An ultraviolet curing resin property measuring apparatus for determining the viscosity or viscoelasticity of a specimen on the basis of a detected torque, comprising:
    a rotating plate supported rotatably about a center axis;
    a torque detection plate disposed on the same axis parallel to the rotating plate, with a given gap left between the two plates;

a torque detection means for detecting a torque exerted on the torque detection plate through the specimen of an ultraviolet curing resin held between the rotating plate and the torque detection plate when the rotating plate is turned;

a total reflection prism, formed of either the rotating plate or the torque detection plate, which is made from a material that has a greater refractive index than the ultraviolet curing resin and transmits ultraviolet light and infrared light;

an ultraviolet irradiation means disposed on the other side of the total reflection prism from the specimen, for directing an ultraviolet beam onto the specimen through the total reflection prism;

an infrared irradiation means for directing an infrared beam into the total reflection prism;

an infrared detection means for detecting the infrared beam emerging from the total reflection prism after total reflection from the interface between the prism and the specimen; and a spectrum analysis means for analyzing the infrared absorption spectrum of the specimen on the basis of the infrared beam detected by the infrared detection means, wherein, while the viscosity or viscoelasticity of the ultraviolet curing resin in the curing process is measured, the spectrum analysis means simultaneously measures the infrared absorption spectrum of the ultraviolet curing resin.

2. The property measuring apparatus according to claim 1, wherein the total reflection prism is moveable from a position on the optical path of the infrared beam directed from the infrared irradiation means, to a position not on the optical path.

3. The property measuring apparatus according to claim 1, wherein the infrared beam is interfering infrared light that is totally reflected from the interface between the total reflection prism and the specimen.

4. An ultraviolet curing resin property measuring apparatus for determining the viscosity or viscoelasticity of a specimen on the basis of a detected torque, comprising:

a rotating plate supported rotatably about a center axis;

a torque detection plate disposed on the same axis parallel to the rotating plate, with a given gap left between the two plates;

a torque detection means for detecting a torque exerted on the torque detection plate through the specimen of an ultraviolet curing resin held between the rotating plate and the torque detection plate when the rotating plate is turned;

a total reflection prism, formed of either the rotating plate or the torque detection plate, which is made from a material that has a greater refractive index than the ultraviolet curing resin and transmits infrared light;

an ultraviolet transmitting plate, formed of the other plate, which is made from a material that transmits ultraviolet light;

an ultraviolet irradiation means disposed on the other side of the ultraviolet transmitting plate from the specimen, for directing an ultraviolet beam onto the specimen through the ultraviolet transmitting plate;

an infrared irradiation means for directing an infrared beam into the total reflection prism;

an infrared detection means for detecting the infrared beam emerging from the total reflection prism after total reflection from the interface between the prism and the specimen; and a spectrum analysis means for analyzing the infrared absorption spectrum of the specimen on the basis of the infrared beam detected by the infrared detection means, wherein, while the viscosity or viscoelasticity of the ultraviolet curing resin in the curing process is measured, the spectrum analysis means simultaneously measures the infrared absorption spectrum of the ultraviolet curing resin.

5. The property measuring apparatus according to claim 4, wherein the composition of the total reflection prism is ZnS.

6. The property measuring apparatus according to claim 4, wherein the total reflection prism s moveable from a position on the optical path of the infrared beam directed from the infrared irradiation means, to a position not on the optical path.

7. The property measuring apparatus according to claim 4, wherein the infrared beam is interfering infrared light that is totally reflected from the interface between the total reflection prism and the specimen.

* * * * *

UNITED STATES PATENT AND TRADEMARK OFFICE
CERTIFICATE OF CORRECTION

PATENT NO. : 8,763,447 B2  
APPLICATION NO. : 13/085563  
DATED : July 1, 2014  
INVENTOR(S) : Toshiyuki Nagoshi et al.

Page 1 of 1

It is certified that error appears in the above-identified patent and that said Letters Patent is hereby corrected as shown below:

In the Claims

In claim 6, column 12, line 35, change "wherein the total reflection prism s moveable" to --wherein the total reflection prism is moveable--.

Signed and Sealed this  
Fourteenth Day of October, 2014

Michelle K. Lee  
*Deputy Director of the United States Patent and Trademark Office*